(12) United States Patent
Mosebach et al.

(10) Patent No.: US 11,058,827 B2
(45) Date of Patent: Jul. 13, 2021

(54) SHROUD LOCK

(71) Applicant: SANOFI-AVENTIS DEUTSCHLAND GMBH, Frankfurt am Main (DE)

(72) Inventors: Carsten Mosebach, Frankfurt am Main (DE); Thomas Mark Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 158 days.

(21) Appl. No.: 15/579,043

(22) PCT Filed: Jun. 2, 2016

(86) PCT No.: PCT/EP2016/062458
§ 371 (c)(1),
(2) Date: Dec. 1, 2017

(87) PCT Pub. No.: WO2016/193352
PCT Pub. Date: Dec. 8, 2016

(65) Prior Publication Data
US 2018/0169349 A1   Jun. 21, 2018

(30) Foreign Application Priority Data

Jun. 3, 2015 (EP) ..................... 15170594

(51) Int. Cl.
*A61M 5/32* (2006.01)
*A61M 5/20* (2006.01)
*A61M 5/315* (2006.01)

(52) U.S. Cl.
CPC ........ *A61M 5/3245* (2013.01); *A61M 5/2033* (2013.01); *A61M 5/3202* (2013.01);
(Continued)

(58) Field of Classification Search
CPC ............. A61M 5/3245; A61M 5/3202; A61M 5/2033; A61M 2005/3267;
(Continued)

(56) References Cited

U.S. PATENT DOCUMENTS

2002/0004647 A1   1/2002   Leong

FOREIGN PATENT DOCUMENTS

CN   103118723   5/2013
CN   104105516   10/2014
(Continued)

OTHER PUBLICATIONS

International Search Report and Written Opinion in International Application No. PCT/EP2016/062458, dated Aug. 11, 2016, 8 pages.

(Continued)

*Primary Examiner* — Theodore J Stigell
(74) *Attorney, Agent, or Firm* — Fish & Richardson P.C.

(57) ABSTRACT

A shroud lock for locking a position of a needle shroud relative to a housing of an autoinjector, includes a shroud beam arranged on the needle shroud and biased radially outwards, a stop arranged within the housing, a recess arranged proximal of the stop, and a cap coupled to the housing and adapted to prevent distal translation of the needle shroud relative to the housing. At least a portion of the shroud beam is within the recess when the cap is in place and, the shroud beam abuts the stop after the needle shroud is locked relative to the housing of the autoinjector. The disclosure further relates to an autoinjector and to a method for assembling such an autoinjector.

17 Claims, 3 Drawing Sheets

(52) U.S. Cl.
CPC ......... *A61M 5/3243* (2013.01); *A61M 5/3157* (2013.01); *A61M 2005/3247* (2013.01); *A61M 2005/3267* (2013.01); *A61M 2205/581* (2013.01)

(58) Field of Classification Search
CPC ........ A61M 2005/3247; A61M 5/3243; A61M 5/3204; A61M 5/3157; A61M 2205/581; A61M 5/3257; A61M 5/326
See application file for complete search history.

(56) References Cited

FOREIGN PATENT DOCUMENTS

| | | | |
|---|---|---|---|
| CN | 104470560 | | 3/2015 |
| EP | 2823841 | * | 1/2015 |
| JP | 2008-220934 | | 9/2008 |
| RU | 2010139938 | | 4/2012 |
| WO | WO 2005/097238 | | 10/2005 |
| WO | WO2012/022810 | * | 2/2012 |
| WO | WO 2012/022810 | | 2/2012 |
| WO | WO 2013/092670 | | 6/2013 |
| WO | WO 2013/167494 | | 11/2013 |
| WO | WO 2015/004052 | | 1/2015 |
| WO | WO 2015/018578 | | 2/2015 |

OTHER PUBLICATIONS

International Preliminary Report on Patentability in International Application No. PCT/EP2016/062458, dated Dec. 5, 2017, 6 pages.

* cited by examiner

SHROUD LOCK

CROSS REFERENCE TO RELATED APPLICATIONS

The present application is the national stage entry of International Patent Application No. PCT/EP2016/062458, filed on Jun. 2, 2016, and claims priority to Application No. EP 15170594.4, filed on Jun. 3, 2015, the disclosures of which are expressly incorporated herein in entirety by reference thereto.

TECHNICAL FIELD

The disclosure relates to a shroud lock and to an autoinjector. The disclosure further relates to a method for assembling an autoinjector.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Furthermore, the force required to push the button/plunger may be too high (e.g., if the user is elderly or a child). And, aligning the injection device, administering the injection, and keeping the injection device still during the injection may require dexterity which some patients (e.g., elderly patients, children, arthritic patients, etc.) may not have.

Autoinjector devices may be single-use or reusable devices and aim to make self-injection easier for patients. A conventional autoinjector may completely or partially replace activities involved in parenteral drug delivery from a manual device. Typically, such activities include removal of a protective syringe cap, insertion of the needle, providing the force for administering the injection and possibly removal and shielding of the used needle. The shielding of a used needle may be achieved by a needle shroud coupled to a lock mechanism for a needle safety shroud lock after the injection.

There remains a need for an improved shroud lock, for an improved autoinjector comprising such a shroud lock and for a method for assembling such an autoinjector.

SUMMARY DISCLOSURE

In certain aspects, an improved shroud lock, an improved autoinjector, and/or a method for assembling such an autoinjector are provided.

Exemplary embodiments of the disclosure are given in the dependent claims.

The present disclosure relates to a shroud lock for locking a position of a needle shroud relative to a housing of an autoinjector. The shroud lock comprises:
 a shroud beam arranged on the needle shroud and biased radially outwards,
 a stop arranged within the housing,
 a recess arranged proximal of the stop, and
 a cap coupled to the housing and adapted to prevent distal translation of the needle shroud relative to the housing. At least a portion of the shroud beam is within the recess when the cap is in place. Furthermore, the shroud beam abuts the stop after the needle shroud is locked relative to the housing of the autoinjector.

The shroud lock provides a needle safety feature for an autoinjector by preventing translation of the needle shroud after the autoinjector is removed from the injection site. The radially outward bias of the shroud beam and the recess in the housing enable the shroud beam to be maintained in a relaxed state during storage to avoid or at least minimize the risk of failure due to creep of material.

In an exemplary embodiment, the needle shroud moves distally from a retracted position towards an extended position relative to the housing when the autoinjector is moved to a locked state. In this extended position, the needle shroud extends beyond a needle of the autoinjector and is locked in an axial position relative to the housing. Thus, a risk of needle-stick injury is reduced.

During the movement of the needle shroud into the extended position, the portion of the shroud beam may deflect radially inwards after passing the recess in a distal direction. Consequently, the shroud beam relaxes radially outwards after passing the stop in the distal direction, which is possible as the cap is no longer present.

In an exemplary embodiment, the needle shroud moves proximally from a pre-extended position towards the retracted position relative to the housing when the autoinjector is pressed against the injection site. The pre-extended position defines an extended position in which the needle shroud is arranged after final assembly before an activation of the autoinjector.

During movement of the needle shroud towards the retracted position, the at least one shroud beam may be moved past the recess in a proximal direction. As a consequence, the shroud beam may be deflected by an inner circumference of the housing. When the shroud beam is proximal of the recess, the needle shroud is in the retracted position.

In an exemplary embodiment, the shroud beam abuts the stop in a relaxed state before final assembly, when the cap is absent. This is a state of the shroud lock before the cap is attached to the autoinjector.

During final assembly, the cap may be coupled to the housing and thus engage and deflect the shroud beam radially inwards out of its abutment with the stop allowing the shroud beam to pass the stop in the proximal direction so the needle shroud is allowed to translate in the proximal direction relative to the housing.

After passing the stop in the proximal direction, the portion of the shroud beam may relax radially outwards into the recess remaining in this state during storage.

In an exemplary embodiment, the shroud lock comprises at least two shroud beams arranged on a distal portion of the needle shroud.

Furthermore, the shroud lock may comprise a number of apertures adapted to interact with the cap for preventing a depression of the needle shroud when the cap is in place, wherein the number of apertures is arranged on the distal portion of the needle shroud as well as the shroud beams.

In a further exemplary embodiment, the needle shroud is coupled to a shroud spring for biasing the needle shroud in a distal direction against the housing.

In an exemplary embodiment, an autoinjector comprises:
 a housing comprising a front part and a rear part, the housing is adapted to receive a syringe, a needle shroud telescoped within the housing,
a cap attached to the front part, and
a shroud lock according to the disclosure.

In an exemplary embodiment, a method for assembling an autoinjector comprises the steps of:

providing a control subassembly, wherein the needle shroud is arranged within the housing locked against movement in the proximal direction due to the shroud beam that abuts the stop, coupling the cap to the housing for engaging the cap to a protective needle sheath, thereby releasing the needle shroud for moving it in the proximal direction by a predetermined distance until the shroud beam is within the recess and the needle shroud is held in a pre-extended state.

In an exemplary embodiment, the shroud beam is deflected radially inwards out of its abutment with the stop when the cap is coupled to the housing.

Furthermore, the cap may be coupled to the housing during or after insertion of the syringe into the control subassembly.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given herein below and the accompanying drawings which are given by way of illustration only, and thus, are not limitative of the present invention, and wherein.

Corresponding parts are marked with the same reference symbols in all figures.

DETAILED DESCRIPTION

Figure 1:
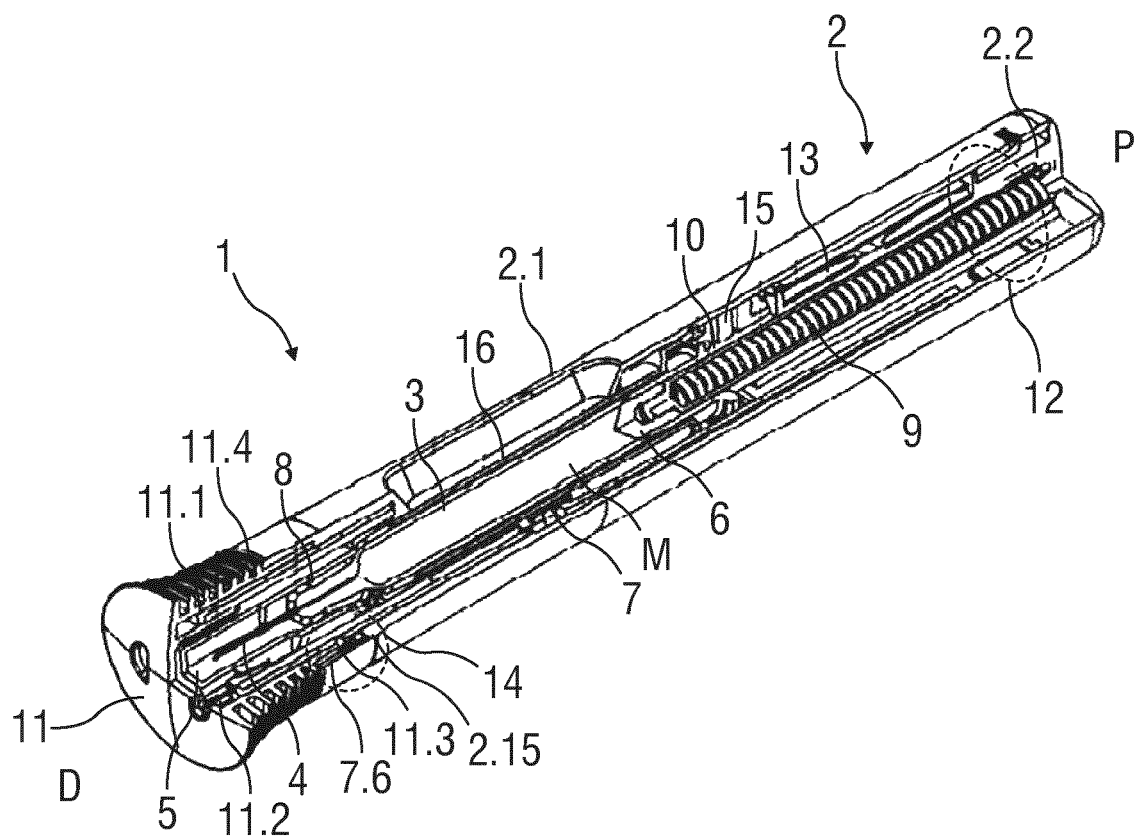
FIG. 1 is a schematic perspective partial section of an exemplary embodiment of an autoinjector according to certain aspects of the present invention.

FIG. 1 is a schematic perspective partial section of an exemplary embodiment of an autoinjector 1 in a state after assembly.

The autoinjector 1 comprises a housing 2 including a sleeve shaped front part 2.1 and a rear part 2.2. The housing 2 is adapted to hold a syringe 3, e.g. a glass syringe. The syringe 3 may be a pre-filled syringe containing a liquid medicament M and have a needle 4 arranged on a distal end. In another exemplary embodiment, the syringe 3 may be a cartridge which includes the medicament M and engages a removable needle (e.g., by threads, snaps, friction, etc.). In the shown exemplary embodiment, the syringe 3 is held in the housing 2 and supported at its proximal end therein.

The autoinjector 1 further comprises a protective needle sheath 5 that is coupled to the needle 4. For example, the protective needle sheath 5 is removably coupled to the needle 4. The protective needle sheath 5 may be a rubber needle sheath or a rigid needle sheath which is composed of rubber and a full or partial plastic shell.

A stopper 6 is arranged for sealing the syringe 3 in a proximal direction P and for displacing the medicament M contained in the syringe 3 through the needle 4.

Figure 2:
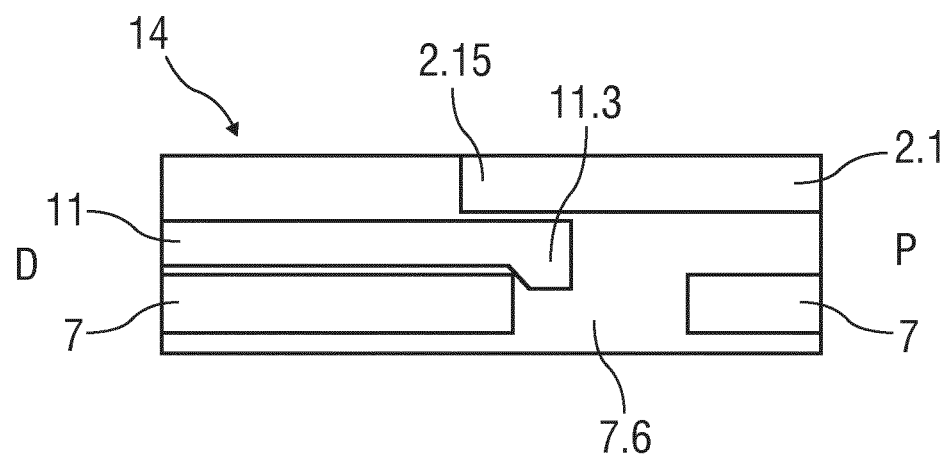
FIG. 2 is a schematic view of an exemplary embodiment of a shroud-pre lock mechanism during assembly.

The autoinjector 1 further comprises a sleeve shaped needle shroud 7 as illustrated in more detail in FIG. 2. In an exemplary embodiment, the needle shroud 7 is telescopically coupled to the housing 2 and movable between an extended position relative to the housing 2 in which the needle 4 is covered and a retracted position relative to the housing 2 in which the needle 4 is exposed. Furthermore, a shroud spring 8 is arranged to bias the needle shroud 7 in a distal direction D against the housing 2.

A drive spring 9 in the shape of a compression spring is arranged within a proximal part of the housing 2, in particular the rear part 2.2. A plunger 10 serves for forwarding the force of the drive spring 9 to the stopper 6. In an exemplary embodiment, the plunger 10 is hollow and the drive spring 9 is arranged within the plunger 10 biasing the plunger 10 in the distal direction D against the rear part 2.2. In another exemplary embodiment, the plunger 10 may be solid and the drive 9 may engage a proximal end of the plunger 10. Likewise, the drive spring 9 could be wrapped around the outer diameter of the plunger 10 and extend within the syringe 3.

Furthermore, the autoinjector 1 comprises a cap 11 that may be removably disposed at a distal end of the housing 2, in particular at a distal end of the front part 2.1. The cap 11 may comprise grip features 11.1 for facilitating removal of the cap 11, e.g., by twisting and/or pulling the cap 11 off the case 2. The cap 11 may further include a grip element 11.2, e.g., a barb, a hook, a narrowed section, etc., arranged to engage the protective needle sheath 5, the housing 2 and/or the needle shroud 7. For example, the protective needle sheath 5 is coupled to the cap 11 in a manner that when the cap 11 is removed, the protective needle sheath 5 is also removed from the needle 4.

A plunger release mechanism 12 is arranged for preventing release of the plunger 10 prior to depression of the needle shroud 7 and for releasing the plunger 10 once the needle shroud 7 is sufficiently depressed.

In an exemplary embodiment, the autoinjector 1 further comprises at least one audible indicator 13 for producing an audible feedback for a user or patient indicating that medicament delivery is complete. In other words: The audible indicator 13 is adapted to indicate to a user or a patient that the full dose of medicament M was spent. The audible indicator 13 is formed for example as a bistable spring and is held in the rear part 2.2.

The rear part 2.2 is adapted to prevent axial movement of the syringe 3 after assembly, in particular during storage, transportation and normal use. In detail, the rear part 2.2 comprises at its front end resilient arms 15. The resilient arms 15 are formed as labyrinth arms to damp impact forces.

To allow an accurate support of the syringe 3 during and after assembly, the autoinjector 1 comprises a carrier 16 adapted to mount and hold the syringe 3 within the housing 2.

A shroud pre-lock mechanism 14 is arranged to prevent depression of the needle shroud 7 when the cap 11 is in place, thus avoiding unintentional activation of the autoinjector 1, e.g. if dropped, during shipping or packaging, etc.

FIG. 2 is a schematic view of the shroud pre-lock mechanism 14 during assembly.

The shroud pre-lock mechanism 14 comprises one, two or more compliant beams 11.3 on the cap 11 and a respective number of apertures 7.6 in the needle shroud 7 adapted to receive each of the compliant beams 11.3. When the cap 11 is attached to the autoinjector 1, the compliant beams 11.3 abut a radial stop 2.15 on the housing 2 which prevents the compliant beams 11.3 from disengaging the apertures 7.6. Furthermore, axial movement of the cap 11 in the proximal direction P relative to the housing 2 is limited by a rib 11.4 on the cap 11 abutting the housing 2. When the cap 11 is pulled in the distal direction D relative to the housing 2, the compliant beams 11.3 abut an edge of the aperture 7.6 and deflect to disengage the aperture 7.6, allowing for removal of the cap 11 and the protective needle sheath 5 attached thereto. In an exemplary embodiment, the compliant beams 11.3 and/or the apertures 7.6 may be ramped to reduce force necessary to disengage the compliant beams 11.3 from the apertures 7.6.

The autoinjector 1 may be further divided in two subassemblies, a control subassembly and a drive subassembly. This allows for improving flexibility as to the time and location of manufacture of the subassemblies and final assembly with the syringe 3.

The control subassembly comprises all parts and mechanisms which control access to the needle 4 and the forces a user will feel when they use the autoinjector 1. The control subassembly comprises the cap 11, the needle shroud 7, the shroud spring 8 and the front part 2.1. In order to assemble the control subassembly, the shroud spring 8 is inserted into the needle shroud 7 and the needle shroud 7 with the shroud spring 8 is inserted into the front part 2.1. The cap 11 is arranged over the distal end of the needle shroud 7.

The drive subassembly comprises the components required to deliver the medicament M. If the viscosity or volume of the medicament M in the syringe 3 is varied, only parts of the drive subassembly may need to be changed. The drive subassembly comprises the plunger 10, the drive spring 9 and the rear part 2.2. The drive subassembly is assembled in a process which requires virtually only axial motion except for the plunger 10. In order to assemble the drive subassembly 1.2 the drive spring 9 is inserted into the plunger 10 and the plunger 10 is inserted in the rear part 2.2 in the proximal direction P, thereby compressing the drive spring 9. Once the plunger 10 reaches a compressed position, it is rotated by an angle, e.g. approximately 30° to lock it to the rear part 2.2. In an exemplary embodiment, the rear part 2.2 could have a cam surface which could induce this rotation prior to the plunger 10 reaching the compressed position.

Figure 3:
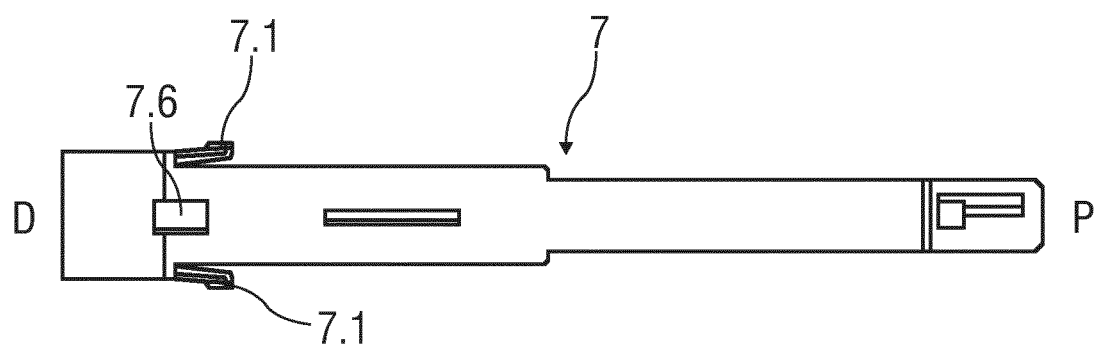
FIG. 3 is a schematic side view of an exemplary embodiment of a needle shroud.

FIG. 3 is a schematic side view of an exemplary embodiment of the needle shroud 7. The figure shows the needle shroud 7 with two shroud beams 7.1 that are part of a shroud lock 17. The shroud beams 7.1 are arranged on a distal section of the needle shroud 7 and are biased radially outwards.

The shroud lock 17 is arranged for locking the needle shroud 7 after removal of the autoinjector 1 from an injection site post-use and for consequently translating the needle shroud 7 in the distal direction D relative to the housing 2 into an extended position post-use.

The shroud lock 17 is shown in more detail in FIGS. 4A to 4E.

FIGS. 4A to 4E are schematic views of the shroud lock 17 in different states.

Figure 4A:
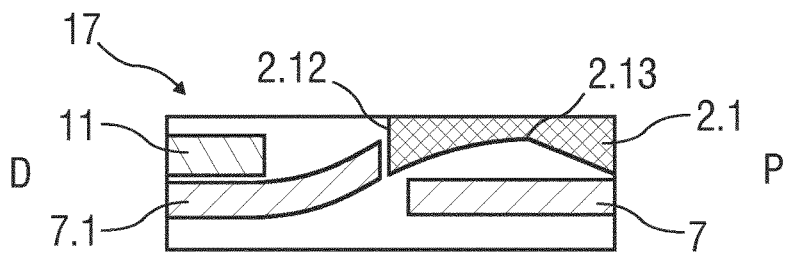
FIGS. 4A to 4E are simplified schematic views of an exemplary embodiment of a needle shroud lock mechanism in different states.

FIG. 4A shows the shroud lock 17 while the autoinjector 1 is in a control subassembly storage state.

The shroud lock 17 comprises at least one of the radially outwardly biased compliant shroud beams 7.1 that proximally abuts a stop 2.12 on the front part 2.1 preventing further movement of the needle shroud 7 in the proximal direction P relative to the front part 2.1 and keeps the control subassembly locked together. Proximal of the stop 2.12, the front part 2.1 comprises a recess 2.13 formed by an increased inner diameter of the front part 2.1.

Figure 4B:
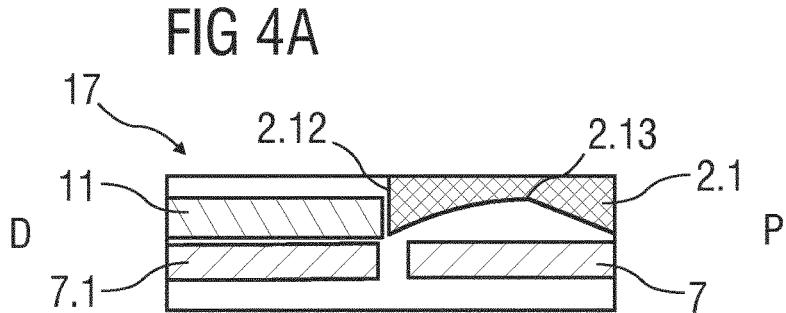

FIG. 4B shows the shroud lock 17 during insertion of the syringe 3 into the control subassembly, wherein the cap 11 is moved in the proximal direction P relative to the front part 2.1 for engaging the protective needle sheath 5 to the cap 11 as it is described in FIG. 2 regarding the shroud pre-lock mechanism 14.

Due to the proximal movement of the cap 11, the compliant shroud beam 7.1 is radially inwardly deflected out of its abutment with the stop 2.12, allowing the shroud beam 7.1 to pass the stop 2.12 in the proximal direction P. Thus, the needle shroud 7 can move further in the proximal direction P relative to the front part 2.1.

Figure 4C:
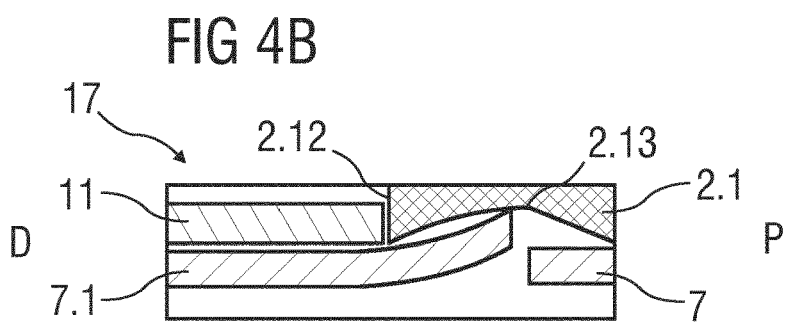

FIG. 4C shows the shroud lock 17 after final assembly of the drive subassembly to the control subassembly.

The needle shroud 7 has been moved further in the proximal direction P relative to the front part 2.1 and the shroud beam 7.1 has relaxed when reaching the recess 2.13. The needle shroud 7 is held in a pre-extended position. A movement of the needle shroud 7 relative to the front part 2.1 is limited by the shroud pre-lock mechanism 14 in order to prevent unintentional activation of the autoinjector 1, e.g. if dropped, during shipping or packaging, etc.

After the final assembly of the drive subassembly to the control subassembly, the autoinjector 1 may be kept in cold chain storage in order to reduce creep in highly stressed components, e.g. under load from the drive spring 9. Due to the fact that the at least one shroud beam 7.1 is in a relaxed state after final assembly, a risk of failure of the autoinjector 1 due to creep of material of the at least one shroud beam 7.1 is minimized.

Figure 4D:
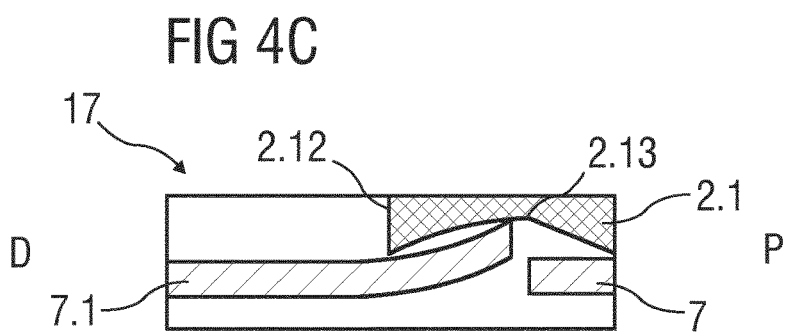

FIG. 4D shows the shroud lock 17 after the cap 11 has been removed, e. g. by pulling it away from the housing 2 in the distal direction D.

By removing the cap 11, the protective needle sheath 5 is removed from the syringe 3 and the needle 4. In order to remove the cap 11 and the protective needle sheath 5, a user needs to overcome a friction force holding the protective needle sheath 5 on the syringe 3 and a force for deflecting the compliant beam 11.3 out of the aperture 7.6 in the needle shroud 7 (not illustrated). The needle shroud 7 is now free to move in the distal direction D relative to the front part 2.1 and the autoinjector 1 is ready to use.

Subsequently, the autoinjector 1 may then be pressed with the needle shroud 7 ahead against an injection site, e. g. a patient's skin, thereby moving the needle shroud 7 proximally from the pre-extended position towards a retracted position against the bias of the shroud spring 8, thus exposing the needle 4 (not illustrated).

After displacing the medicament M from the syringe 3, the user may remove the autoinjector 1 from the injection site. Consequently, the needle shroud 7 moves from the retracted position into the extended position driven by the shroud spring 8, thus obscuring the needle 4.

Figure 4E:
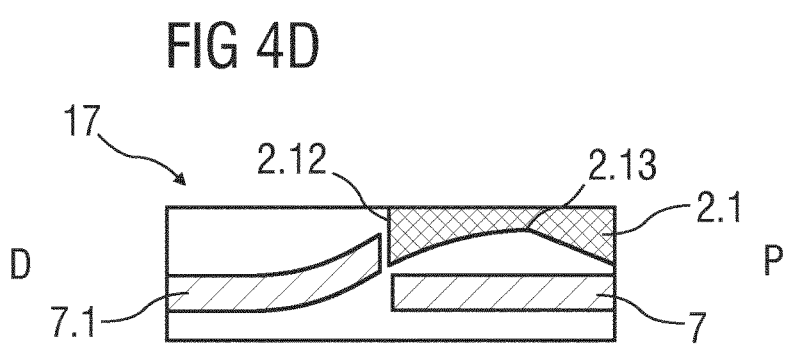

FIG. 4E shows the shroud lock 17 after the autoinjector 1 has been removed from the injection site post-delivery.

By removing the autoinjector 1 from the injection site, the needle shroud 7 moves into the distal direction D relative to the housing 2. The shroud beam 7.1 deflects inwardly due to the tapered inner diameter of the front part 2.1 in the distal direction D. After passing the stop 2.12 distally, the shroud beam 7.1 relaxes radially outwards abutting the stop 2.12 again which is possible as the cap 11 is no longer present. Afterwards, the shroud beam 7.1 cannot return in the proximal direction P as it would hit the stop 2.12. The needle shroud 7 is thus locked in the extended position. Further extension of the needle shroud 7 may be prevented by a case boss on the housing 2 engaging with a shroud boss in the needle shroud 7 (not illustrated). The risk of post-injection needle stick injury is thus reduced.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

LIST OF REFERENCES 1 autoinjector
2 housing
2.1 front part
2.2 rear part
2.12 stop
2.13 recess
2.15 radial stop
3 syringe
4 needle
5 protective needle sheath
6 stopper
7 needle shroud
7.1 shroud beam
7.6 aperture
8 shroud spring
9 drive spring
10 plunger
11 cap
11.1 grip feature
11.2 grip element
11.3 compliant beam
11.4 rib
12 plunger release mechanism
13 audible indicator
14 shroud pre-lock mechanism
15 resilient arm
16 carrier
17 shroud lock
D distal direction
M medicament
P proximal direction

The invention claimed is:

1. A shroud lock for locking a position of a needle shroud of an autoinjector relative to a housing of the autoinjector, the shroud lock comprising:
a shroud beam arranged on the needle shroud and biased radially outwards;
a stop arranged within the housing;
a recess arranged proximal of the stop; and
a cap coupled to the housing and adapted to prevent distal translation of the needle shroud relative to the housing,
wherein at least a portion of the shroud beam is configured to be within the recess when the cap is in place over a distal portion of the autoinjector, and
wherein the shroud beam is configured to abut the stop after the needle shroud is locked relative to the housing of the autoinjector.

2. The shroud lock according to claim 1, wherein the shroud lock is configured to lock the needle shroud and move the needle shroud distally from a retracted position towards an extended position relative to the housing when the autoinjector is moved to a locked state.

3. The shroud lock according to claim 2, wherein, during movement of the needle shroud into the extended position, the portion of the shroud beam is configured to deflect radially inwards after passing the recess in a distal direction and the shroud beam is configured to relax radially outwards after passing the stop in the distal direction.

4. The shroud lock according to claim 2, wherein the needle shroud is configured to move proximally from a pre-extended position towards the retracted position relative to the housing when the autoinjector is pressed against an injection site.

5. The shroud lock according to claim 4, wherein, during movement of the needle shroud towards the retracted position, the portion of the shroud beam is configured to be moved past the recess in a proximal direction.

6. The shroud lock according to claim 2, wherein the shroud beam is configured to abut the stop in a relaxed state before final assembly and when the cap is absent.

7. The shroud lock according to claim 6, wherein, during the final assembly, the cap is configured to be coupled to the housing such that the cap engages and deflects the shroud beam radially inwards out of its abutment with the stop allowing the shroud beam to pass the stop in a proximal direction.

8. The shroud lock according to claim 7, wherein the portion of the shroud beam is configured to relax radially outwards into the recess after passing the stop in the proximal direction.

9. The shroud lock according to claim 2, further comprising at least two shroud beams arranged on a distal portion of the needle shroud.

10. The shroud lock according to claim 9, further comprising apertures adapted to interact with the cap for preventing a depression of the needle shroud when the cap is in place over the distal portion of the autoinjector, wherein the apertures are arranged on the distal portion of the needle shroud.

11. An autoinjector comprising:
a housing comprising a front part and a rear part, the housing is adapted to receive a syringe;
a needle shroud telescoped within the housing;
a cap attached to the front part; and
a shroud lock comprising
a shroud beam arranged on the needle shroud and biased radially outwards;
a stop arranged within the housing; and
a recess arranged proximal of the stop,
wherein the cap is adapted to prevent distal translation of the needle shroud relative to the housing,
wherein at least a portion of the shroud beam is configured to be within the recess when the cap is in place, and
wherein the shroud beam is configured to abut the stop after the needle shroud is locked relative to the housing of the autoinjector.

12. The autoinjector according to claim 11, wherein the shroud lock is configured to lock the needle shroud and move the needle shroud distally from a retracted position towards an extended position relative to the housing when the autoinjector is moved to a locked state.

13. The autoinjector according to claim 12, wherein, during movement of the needle shroud into the extended position, the portion of the shroud beam is configured to deflect radially inwards after passing the recess in a distal direction and the shroud beam is configured to relax radially outwards after passing the stop in the distal direction.

14. The autoinjector according to claim 12, wherein the needle shroud is configured to move proximally from a pre-extended position towards the retracted position relative to the housing when the autoinjector is pressed against an injection site.

15. The autoinjector according to claim 14, wherein, during movement of the needle shroud towards the retracted position, the portion of the shroud beam is configured to be moved past the recess in a proximal direction.

16. The autoinjector according to claim 12, wherein the shroud beam is configured to abut the stop in a relaxed state before final assembly and when the cap is absent.

17. The autoinjector according to claim 12, wherein the needle shroud is coupled to a shroud spring for biasing the needle shroud in a distal direction against the housing.

* * * * *